(12) United States Patent
Tang et al.

(10) Patent No.: US 11,361,865 B2
(45) Date of Patent: *Jun. 14, 2022

(54) COMPUTER AIDED MEDICAL METHOD AND MEDICAL SYSTEM FOR MEDICAL PREDICTION

(71) Applicant: HTC Corporation, Taoyuan (TW)

(72) Inventors: Kai-Fu Tang, Taoyuan (TW); Edward Chang, Taoyuan (TW); Hao-Cheng Kao, Taoyuan (TW)

(73) Assignee: HTC Corporation, Taoyuan (TW)

( * ) Notice: Subject to any disclaimer, the term of this patent is extended or adjusted under 35 U.S.C. 154(b) by 227 days.

This patent is subject to a terminal disclaimer.

(21) Appl. No.: 16/920,454

(22) Filed: Jul. 3, 2020

(65) Prior Publication Data

US 2020/0342989 A1 Oct. 29, 2020

Related U.S. Application Data

(63) Continuation of application No. 15/835,479, filed on Dec. 8, 2017, now Pat. No. 10,734,113.

(Continued)

(51) Int. Cl.
*G16H 50/20* (2018.01)
*G06N 20/00* (2019.01)

(Continued)

(52) U.S. Cl.
CPC ............. *G16H 50/20* (2018.01); *G06N 3/006* (2013.01); *G06N 5/04* (2013.01); *G06N 20/00* (2019.01); *G16H 50/50* (2018.01); *G16H 50/70* (2018.01)

(58) Field of Classification Search
CPC ........ G16H 50/20; G16H 50/30; G16H 50/50; G16H 50/00
See application file for complete search history.

(56) References Cited

U.S. PATENT DOCUMENTS 6,468,210 B1 10/2002 Iliff
6,684,276 B2 1/2004 Walker et al.
(Continued)

FOREIGN PATENT DOCUMENTS

CN 1423789 A 6/2003
CN 102110192 A 6/2011
(Continued)

OTHER PUBLICATIONS

Corresponding Taiwan office action dated Oct. 2, 2018.
(Continued)

*Primary Examiner* — Joseph D Burgess
(74) *Attorney, Agent, or Firm* — CKC & Partners Co., LLC

(57) ABSTRACT

A computer aided medical method includes the following steps. An initial symptom of a patient and context information is collected through an interaction interface. Actions in a series are sequentially generated according to the candidate prediction models and the initial symptom. Each of the actions corresponds to one of the inquiry actions or one of the disease prediction actions. If the latest one of the sequential actions corresponds to one of the disease prediction actions, potential disease predictions are generated in a first ranking evaluated by the candidate prediction models. The first ranking is adjusted into a second ranking according to the context information. A result prediction corresponding to the potential disease predictions is generated in the second ranking.

20 Claims, 10 Drawing Sheets

Related U.S. Application Data

(60) Provisional application No. 62/520,642, filed on Jun. 16, 2017.

(51) Int. Cl.
*G16H 50/70* (2018.01)
*G06N 3/00* (2006.01)
*G06N 5/04* (2006.01)
*G16H 50/50* (2018.01)

(56) References Cited

U.S. PATENT DOCUMENTS

| | | | |
|---|---|---|---|
| 7,149,756 | B1 | 12/2006 | Schmitt et al. |
| 9,081,879 | B2 | 7/2015 | Iliff |
| 2002/0002325 | A1* | 1/2002 | Iliff .................. G16H 50/20 600/300 |
| 2005/0065813 | A1 | 3/2005 | Mishelevich et al. |
| 2006/0135859 | A1* | 6/2006 | Iliff .................. G16H 50/20 128/920 |
| 2008/0021288 | A1 | 1/2008 | Bowman et al. |
| 2009/0259494 | A1 | 10/2009 | Feder et al. |
| 2013/0268203 | A1 | 10/2013 | Pyloth |
| 2014/0249830 | A1 | 9/2014 | Gallopyn et al. |
| 2016/0196402 | A1 | 7/2016 | Higashi |
| 2017/0103174 | A1 | 4/2017 | Kim et al. |

FOREIGN PATENT DOCUMENTS

| | | |
|---|---|---|
| CN | 103164616 A | 6/2013 |
| CN | 103366073 A | 10/2013 |
| CN | 105095622 A | 11/2015 |
| CN | 105190634 A | 12/2015 |
| CN | 105447299 A | 3/2016 |
| CN | 106354998 A | 1/2017 |
| CN | 106599574 A | 4/2017 |
| CN | 106709254 A | 5/2017 |
| TW | 200532523 A | 10/2005 |
| TW | 201142641 A | 12/2011 |
| TW | 201327460 A | 7/2013 |

OTHER PUBLICATIONS

Corresponding Taiwan office action dated Oct. 24, 2018.
Corresponding Taiwan office action dated Feb. 21, 2019.
Corresponding Taiwan office action dated Jul. 10, 2019.
Corresponding Chinese office action dated Jul. 22, 2020.
Office Action of the related U.S. Appl. No. 15/826,626 dated Dec. 20, 2019.
Office Action of the related U.S. Appl. No. 15/826,626 dated Apr. 22, 2020.
Aslakson et al. "Live Sequence Charts to Model Medical Information." (Jun. 15, 2012). Theoretical Biology and Medical Modelling 2012 9:22. (Year: 2012).
"Deep Reinforcement Learning Demystified (Episode 2)—Policy Iteration, Value Iteration and Q-learning"; Alzantot; Jul. 9, 2017 (Year:2017).
"Reinforcement Learning"; Woergoetter et al.; 2008 (Year: 2008).
Kai-Fu Tang et al., "Inquire and Diagnose: Neural Symptom Checking Ensemble using Deep Reinforcement Learning", Deep Reinforcement Learning Workshop NIPS 2016, URL: https://sites.google.com/site/deeprlnips2016/, Dec. 9, 2016, Contributed Papers, Barcelona, Spain, p. 1-9.

\* cited by examiner

COMPUTER AIDED MEDICAL METHOD AND MEDICAL SYSTEM FOR MEDICAL PREDICTION

RELATED APPLICATIONS

The present application is a continuation application of the U.S. application Ser. No. 15/835,479, filed Dec. 8, 2017, which claims priority to U.S. Provisional Application Ser. No. 62/520,642, filed Jun. 16, 2017, all of which are herein incorporated by reference.

BACKGROUND

Field of Invention

The disclosure relates to a computer aided medical method. More particularly, the disclosure relates to a computer aided medical method for generating a medical prediction.

Description of Related Art

Recently the concept of computer-aided medical system has emerged in order to facilitate self-diagnosis for patients. The computer aided medical system may request patients to provide some information, and then the computer aided medical system may provide a diagnosis of the potential diseases based on the interactions with those patients.

SUMMARY

The disclosure provides a computer aided medical method. The computer aided medical method is based on a plurality of candidate prediction models. Each of the candidate prediction models comprises a plurality of inquiry actions and a plurality of disease prediction actions. The computer aided medical method includes the following steps. An initial symptom and context information are obtained. Actions in a series are sequentially generated according to the candidate prediction models and the initial symptom. Each of the actions corresponds to one of the inquiry actions or one of the disease prediction actions. In response to that the latest one of the sequential actions corresponds to one of the disease prediction actions, potential disease predictions are generated in a first ranking evaluated by the candidate prediction models. The first ranking is adjusted into a second ranking according to the context information. A list of the potential disease predictions is generated in the second ranking.

The disclosure also provides a non-transitory computer readable storage medium with a computer program. The computer program is configured to execute aforesaid computer aided medical method.

The disclosure also provides a medical system, which is based on a plurality of candidate prediction models. Each of the candidate prediction models comprises a plurality of inquiry actions and a plurality of disease prediction actions. The medical system comprises an interaction interface and a control circuit. The interaction interface is configured for collecting an initial symptom. The control circuit is communicated with the interaction interface. The control circuit is operable to sequentially generate a series of actions according to the candidate prediction models and the initial symptom. Each of the actions corresponding to one of the inquiry actions or one of the disease prediction actions. In response to that the latest one of the sequential actions corresponding to one of the disease prediction actions, the control circuit is operable to generate a plurality of potential disease predictions in a first ranking evaluated by the candidate prediction models. The control circuit is operable to adjust the first ranking into a second ranking according to context information. The control circuit is operable to generate a list of the potential disease predictions in the second ranking.

It is to be understood that both the foregoing general description and the following detailed description are demonstrated by examples, and are intended to provide further explanation of the invention as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1:
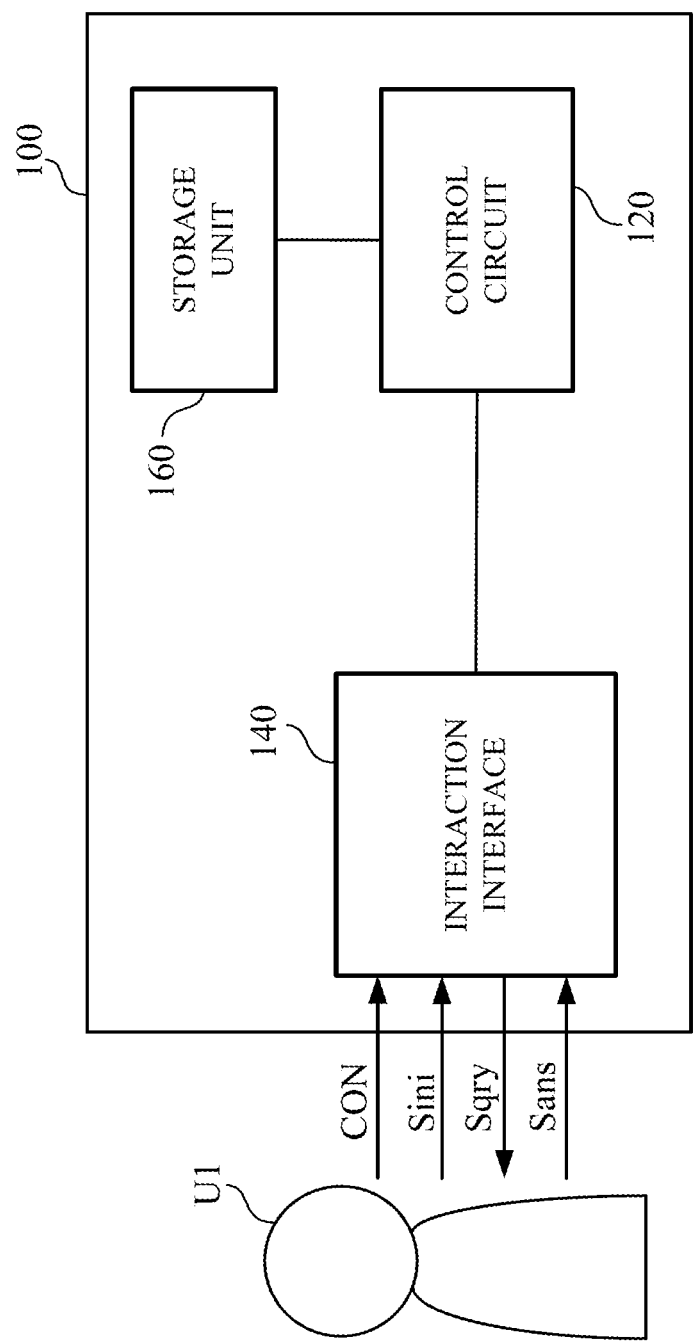
FIG. 1 is a schematic diagram illustrating a medical system according to an embodiment of the disclosure.

Reference will now be made in detail to the present embodiments of the disclosure, examples of which are illustrated in the accompanying drawings. Wherever possible, the same reference numbers are used in the drawings and the description to refer to the same or like parts.

Reference is made to FIG. 1, which is a schematic diagram illustrating a medical system 100 according to an embodiment of the disclosure. The medical system 100 includes a control circuit 120, an interaction interface 140 and a storage unit 160.

In some embodiments, the control circuit 120 is communicated with the interaction interface 140. The medical system 100 is configured to interact with the user U1 through the interaction interface 140 (e.g. obtaining at least one initial symptom from the user U1, providing some symptom inquiries to the user U1 and/or obtaining corresponding symptom responses from the user U1). Based on aforesaid interaction history, the medical system 100 is able to analyze, diagnose or predict a potential disease occurring to the user U1. The medical system 100 is trained with a machine learning algorithm, such that the medical system 100 is capable to inquire and diagnose based on limited patient data. In some embodiments, the medical system 100 adopts a reinforcement learning (RL) framework to formulate inquiry and diagnosis policies.

In some embodiments, the medical system 100 is established with a computer, a server or a processing center. The control circuit 120 can be implemented by a processor, a central processing unit or a computation unit. The interaction interface 140 can include an output interface (e.g., a display panel for display information) and an input device (e.g., a touch panel, a keyboard, a microphone, a scanner or a flash memory reader) for user to type text commands, to give voice commands or to upload some related data (e.g., images, medical records, or personal examination reports).

In some other embodiments, at least a part of the medical system 100 is established with a distribution system. For example, the control circuit 120 is established by a cloud computing system. In this case, the interaction interface 140 can be a smart phone, which is communicated with the control circuit 120 by wireless. The output interface of the interaction interface 140 can be a display panel on the smart phone. The input device of the interaction interface 140 can be a touch panel, a keyboard and/or a microphone on the smart phone.

As shown in FIG. 1, the storage unit 160 is coupled with the control circuit 140. In some embodiments, the storage unit 160 can be implemented by a memory, a flash memory, a ROM, a hard drive or any equivalent storage component.

As shown in FIG. 1, the interaction interface 140 can be manipulated by a user U1. The user U1 can see the information displayed on the interaction interface 140 and the user U1 can enter his/her inputs on the interaction interface 140. In an embodiment, the interaction interface 140 will display a notification to ask the user U1 about his/her symptoms. The symptom inputted by the user U1 will be regarded as initial symptom Sini (e.g., one or more symptoms inputted by the user U1). The interaction interface 140 is configured for obtaining the initial symptom Sini and context information CON according to the user's manipulation. The interaction interface 140 transmits the initial symptom Sini and the context information CON to the control circuit 120.

The control circuit 120 is configured for generating symptom inquiries Sqry to be displayed on the interaction interface 140 according to the initial symptom Sini. The symptom inquiries Sqry are displayed on the interaction interface 140 sequentially, and the user U1 can answer the symptom inquiries Sqry through the interaction interface 140. The interaction interface 140 is configured for receiving symptom responses Sans corresponding to the symptom inquiries Sqry. When the control circuit 120 obtains enough information to make a decision, the control circuit 120 is configured to generate a result prediction, such as at least one disease prediction (e.g., a disease name or a list of disease names ranked by their probabilities) or/and at least one medical department suggestion matching the possible disease according to the initial symptom Sini and the responses Sans. The control circuit 120 will decide optimal questions (i.e., the symptom inquiries Sqry) to ask the user U1 according to the initial symptom Sini and all previous responses Sans (before the current question). The optimal questions are selected according to a prediction model utilized by the control circuit 120 in order to increase efficiency (e.g., the result prediction can be decided faster or in fewer inquiries) and the correctness (e.g., the result prediction can be more accurate) of the result prediction.

Figure 2:
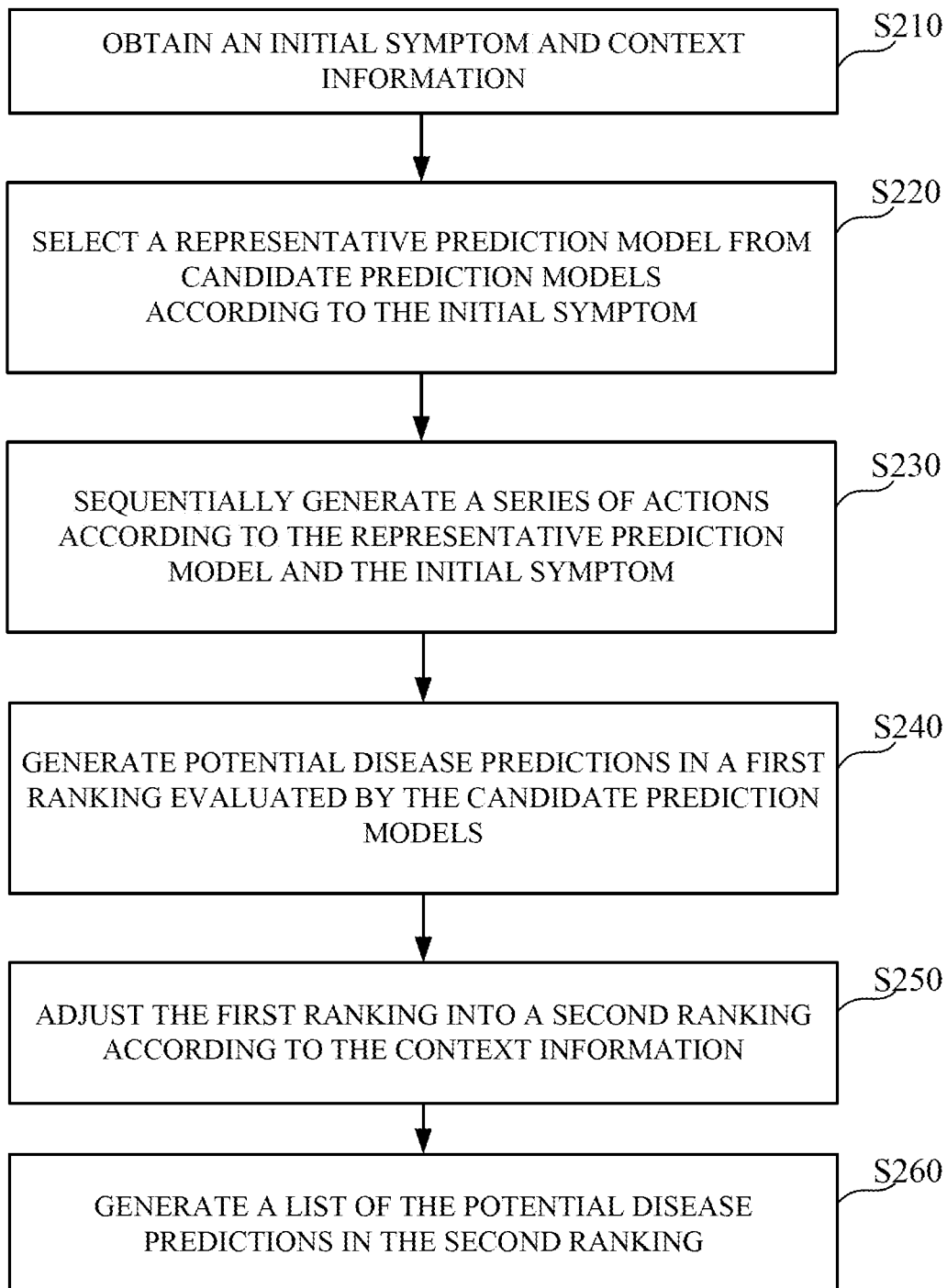
FIG. 2 is a flow chart illustrating a computer aided medical method according to an embodiment of the disclosure.

Reference is further made to FIG. 2, which is a flow chart illustrating a computer aided medical method 200 according to an embodiment of the disclosure. The computer aided medical method 200 can be performed by the medical system 100 in FIG. 1.

As shown in FIG. 1 and FIG. 2, operation S210 is performed to obtain the initial symptom Sini and context information CON. About the initial symptom Sini, the interaction interface 140 may show a text notification read as "How do you feel today? If you don't feel well, can you describe your feeling in a few words?" The user U1 may reply the question by typing (or inputting by voice recognition) an input as "I suffer severe headache right now." In this example, the initial symptom Sini (e.g., headache) can be recognized in the input from the user U1. In an embodiment the context information CON can be obtained through the interaction interface 140 according to inputs from the user U1. In another embodiment, the context information CON can be obtained by the medical system 100 by downloading or fetching from a medical record database in a hospital or a medical organization. For example, the user U1 can provide a personal identification or personal information to create an account on the medical system 100. In this example, the medical system 100 can download or fetch the context information CON of the user U1 from the medical record database automatically, if the user U1 authorizes the medical system 100 doing so.

In some cases, some computer aided medical system will establish a monolithic prediction model to analyze inputs from patients and generate the prediction. However, it takes a lot of computations to establish the monolithic prediction model because the monolithic prediction model should cover all kinds of diseases and symptoms. The monolithic prediction model may take a long time to make the prediction, and the prediction made by the monolithic prediction model may not be accurate sometime. In addition, it is difficult to train the monolithic prediction model because there are too many diseases and symptoms should be considered by the monolithic prediction model. Even in a hospital, there are many doctors specialized in different medical departments. It is hard for one doctor to diagnose all kinds of symptoms and diseases with high efficiency and high accuracy.

Figure 3:
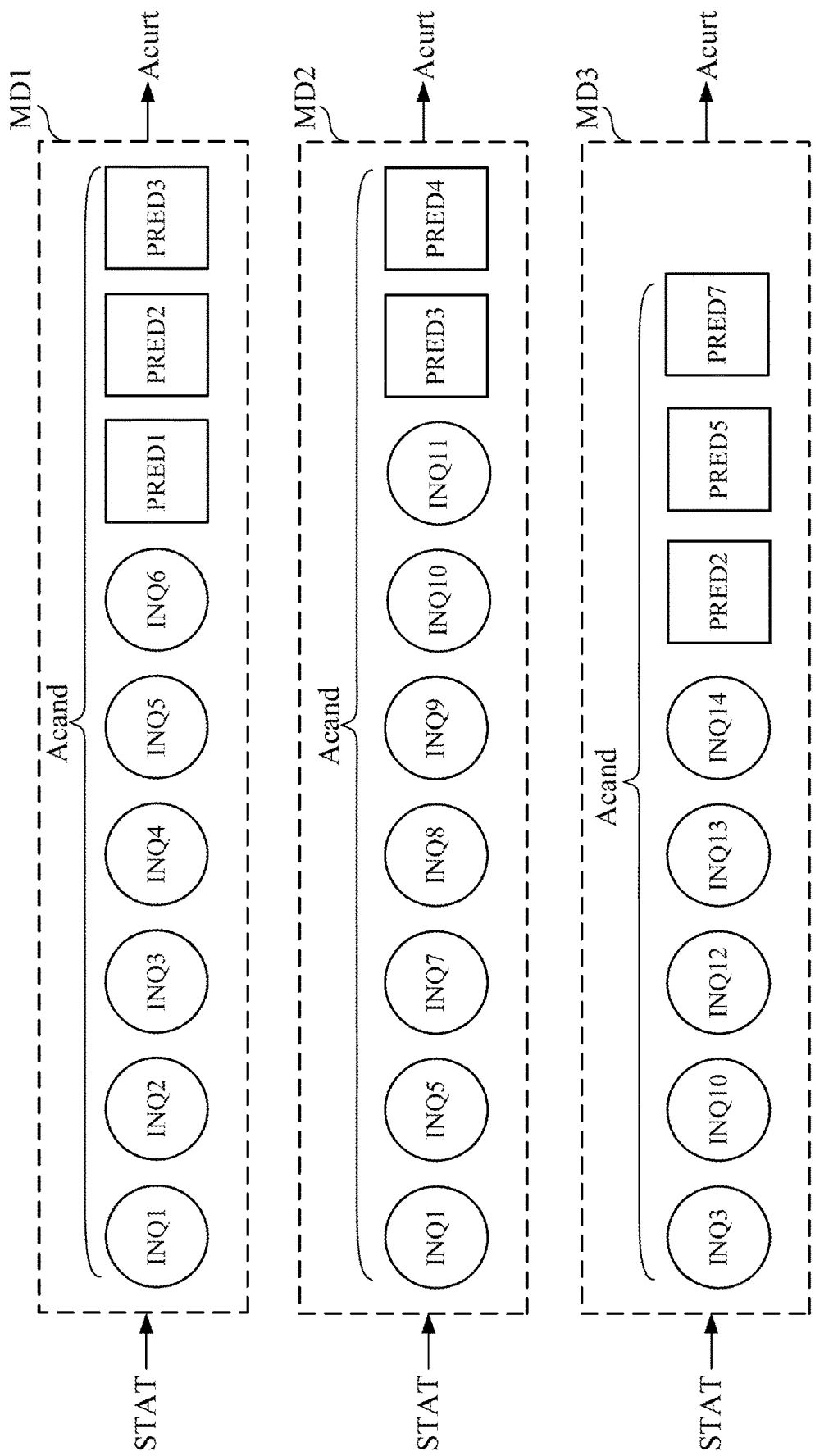
FIG. 3 is a schematic diagram illustrating different candidate prediction models established according to an embodiment of the disclosure.

To mimic real doctors in different hospital departments, the medical system 100 utilizes multiple candidate prediction models trained by a machine learning algorithm according to clinical data. Reference is further made to FIG. 3, which is a schematic diagram illustrating different candidate prediction models MD1, MD2 and MD3 established according to an embodiment of the disclosure. In some embodiments, the candidate prediction models MD1, MD2 and MD3 are trained independently corresponding to different anatomical parts of a human body. In some other embodiments, the candidate prediction models MD1, MD2 and MD3 are trained independently corresponding to different functional parts (e.g., respiratory system, digestive system, nervous system, endocrine system) of a human body. Each one of the candidate prediction models MD1, MD2 and MD3 is not required to cover all diseases and symptoms over the human body. The combination of the candidate prediction models MD1, MD2 and MD3 shall be able to cover all diseases and symptoms on different anatomical parts or different functional parts over the human body.

Each of the candidate prediction models MD1, MD2 and MD3 is trained according to clinical data related to one anatomical part of the human body. The clinical data includes clinical records from some medical databases, such as data and information from the Centers for Disease Control and Prevention. Each clinical record describes a relationship between a diagnosed disease and corresponding symptoms of the diagnosed disease. For example, a patient who has the disease of venous insufficiency may have the symptoms of skin lesion, leg swelling and leg pain; another patient who has the disease of fracture of arm may have the symptoms of arm pain, wrist swelling, elbow stiffness or tightness; and, still another patient who has the disease of chronic constipation may have the symptoms of sharp abdominal pain, pain of the anus and stomach bloating. The clinical records about different diseases and symptoms are grouped into different anatomical parts (or different functional parts).

A computation time for training one of the candidate prediction models MD1, MD2 or MD3 will be much shorter than a computation time for training the monolithic prediction model, because the one of the candidate prediction models MD1, MD2 or MD3 shall consider diseases and symptoms related to one anatomical part (or one functional part). In addition, the candidate prediction models MD1, MD2 and MD3 can be trained individually in parallel computing, such that it will be faster to establish the candidate prediction models MD1, MD2 and MD3 than to establish the monolithic prediction model.

Each of the candidate prediction models MD1, MD2 and MD3 is trained with the clinical data related to one anatomical part (or one functional part). For example, the candidate prediction model MD1 is trained with the clinical data related to head; the candidate prediction model MD2 is trained with the clinical data related to chest; and, the candidate prediction model MD3 is trained with the clinical data related to arm. The candidate prediction models utilized in the medical system 100 and the computer aided medical method 200 are not limited to three models as shown in FIG. 2. For brevity, FIG. 2 is a demonstrational example to illustrate three candidate prediction models MD1, MD2 and MD3. The candidate prediction models utilized in the medical system 100 and the computer aided medical method 200 can be two or more different models.

In an embodiment, the human body can be classified into eleven different groups (respectively corresponding to different anatomical parts), such as head, neck, arm, chest, abdomen, back, pelvis, buttock, leg, skin, and general area on the human body. The group of "general area" corresponds to diseases and symptoms which are not only affect one anatomical part on the human body. In this embodiment, the medical system 100 and the computer aided medical method 200 will train eleven candidate prediction models corresponding to these eleven groups. For brevity, the following paragraphs are explained with the embodiment including three candidate prediction models MD1, MD2 and MD3 as shown in FIG. 3.

In another embodiment, the human body can be classified into different groups (respectively corresponding to functional parts), such as respiratory system, digestive system, nervous system, endocrine system, musculoskeletal system, circulatory system, urinary system, reproductive system and general function (which means the symptom does not occur to one particular functional part) on the human body.

The initial symptom Sini (e.g., one or more symptoms inputted from the user U1) will provide an important clue about how the user U1 feels. The control circuit 120 is able to determine which one of the candidate prediction models MD1, MD2 or MD3 is suitable to predict the situation of the user U1. As shown in FIG. 1 and FIG. 2, operation S220 is performed to select a representative prediction model from the candidate prediction models MD1-MD3 according to the initial symptom Sini.

For example, if the initial symptom Sini is "headache", the candidate prediction model MD1 (corresponding to the head) can be selected from the candidate prediction models MD1-MD3 as the representative prediction model. On the other hand, if the initial symptom Sini is "short breathing", the candidate prediction model MD2 (corresponding to the chest) can be selected from the candidate prediction models MD1-MD3 as the representative prediction model.

As shown in FIG. 1 and FIG. 2, operation S230 is performed to sequentially generate a series of actions according to the representative prediction model and the initial symptom Sini. The actions in a series are generated corresponding to a plurality of candidate actions in the representative prediction model.

As shown in FIG. 3, if the candidate prediction model MD1 is selected as the representative prediction model, the candidate prediction model MD1 includes several candidate actions Acand. Two types of candidate actions Acand existed in the candidate prediction model MD1 include inquiry actions INQ1, INQ2, INQ3, INQ4, INQ5 and INQ6 and disease prediction actions PRED1, PRED2 and PRED3. Two types of candidate actions Acand existed in the candidate prediction model MD2 include inquiry actions INQ1, INQ5, INQ7, INQ8, INQ9, INQ10 and INQ11 and disease prediction actions PRED3 and PRED4. Two types of candidate actions Acand existed in the candidate prediction model MD3 include inquiry actions INQ3, INQ10, INQ12, INQ13, INQ14 and disease prediction actions PRED2, PRED5 and PRED7. Each of the actions in the series is one of the inquiry actions INQ1-INQ14 or the disease prediction actions PRED1-PRED7. In some embodiments, the actions in the series are displayed on the interaction interface 140.

Each of the inquiry actions INQ1-INQ14 is to ask a question about whether the user suffers a specific symptom (e.g., "Do you cough?", "Do you have fever?", "Can you sleep well?" and "Do you suffer short breathing"). When the user U1 provides answers (e.g., the answers can be simply a yes/no responses) to the inquiry actions INQ1-INQ14, the control circuit 120 will acknowledge more information about the user U1. When the information about the user U1 is enough to make a prediction, the control circuit 120 will select one disease prediction action according to the initial symptom Sini, all previous inquiry actions and all symptom responses Sans prior to the prediction. In some embodiments, each of the disease prediction actions PRED1-PRED7 corresponds to one disease.

If the candidate prediction model MD1 is selected as the representative prediction model, the candidate prediction model MD1 is utilized by the control circuit 120 to select one of the candidate actions Acand according to a current state STAT, and the one of the candidate action is selected to be the current action Acurt. When one of the inquiry actions INQ1-INQ6 is selected as the current action Acurt, the medical system 100 and the computer aided medical method 200 will perform the selected one of the inquiry actions INQ1-INQ6. When one of the disease prediction actions PRED1, PRED2 and PRED3 is selected as the current action Acurt, the medical system 100 and the computer aided medical method 200 will make a disease prediction.

Figure 4:
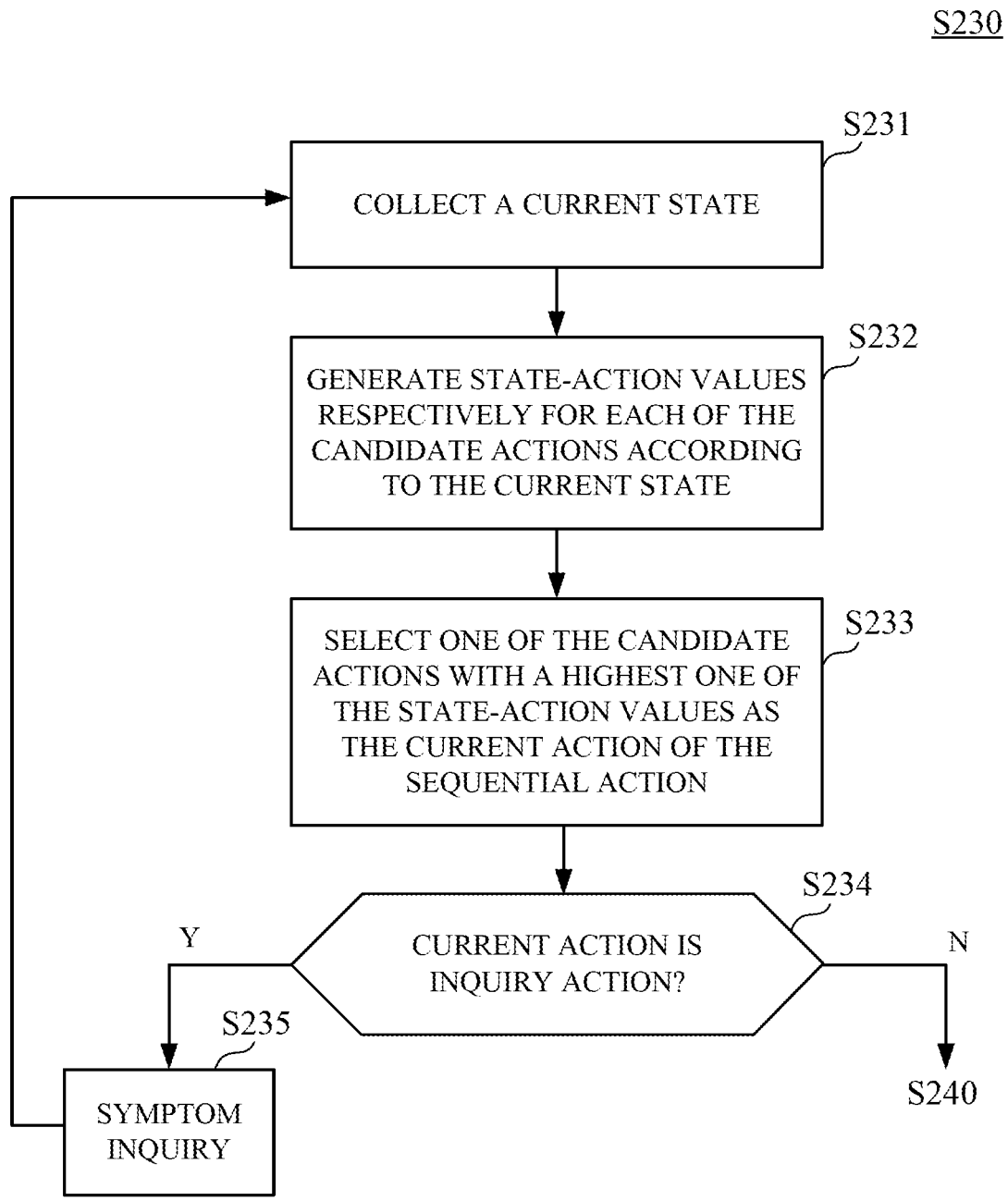
FIG. 4 is a flow chart illustrating further steps performed in one step in FIG. 2.

Reference is further made to FIG. 4, which is a flow chart illustrating further steps performed in the step S230 in FIG. 2. As the embodiment shown in FIG. 4, the step S230 can further include steps S231-S235. The steps S231-S235 include further details about how to generate a series of actions according to the representative prediction model and the initial symptom Sini.

Figure 5A:
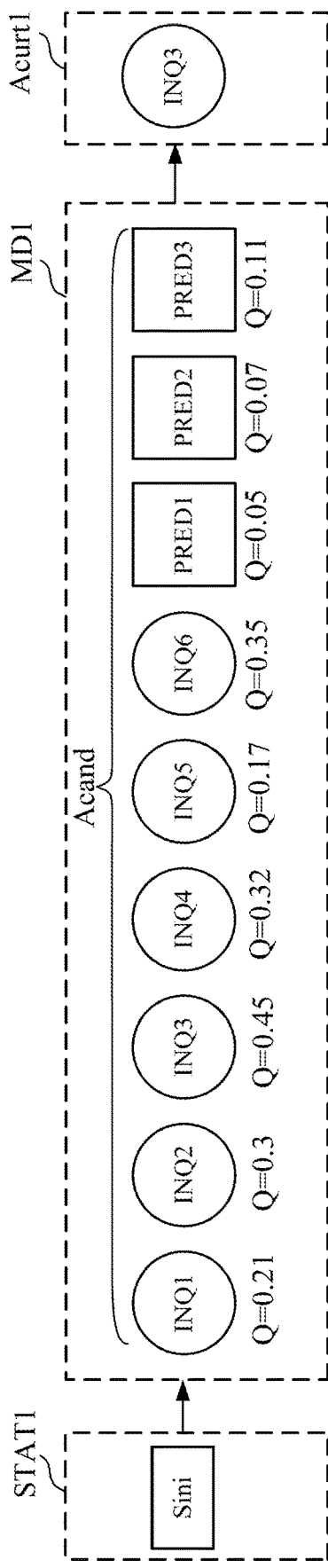
FIG. 5A to FIG. 5C are schematic diagrams illustrating a demonstrational example about how to generate the sequential actions in different stages.
Figure 5B:
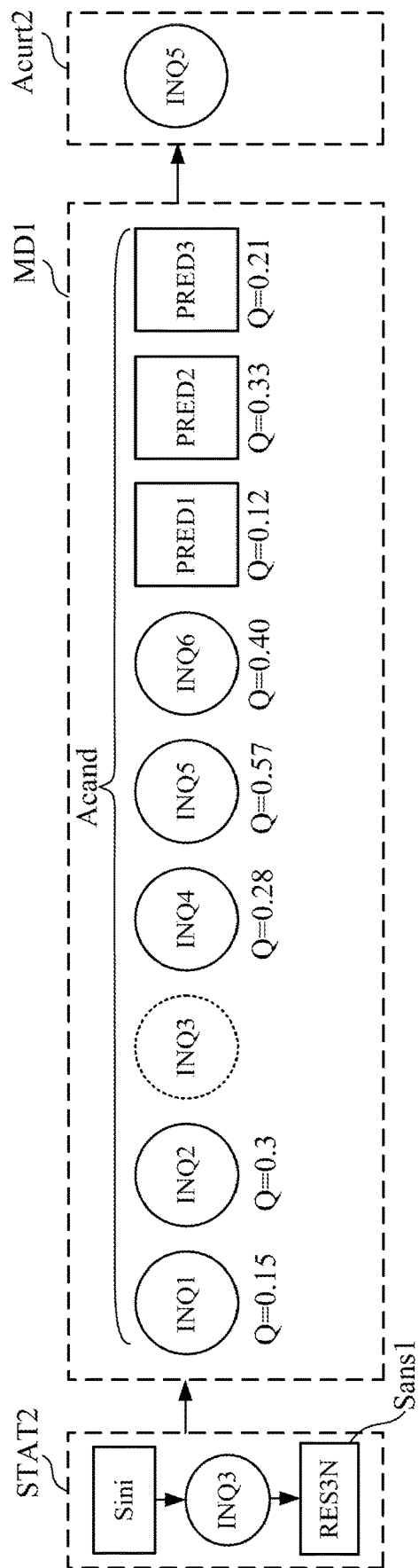
Figure 5C:
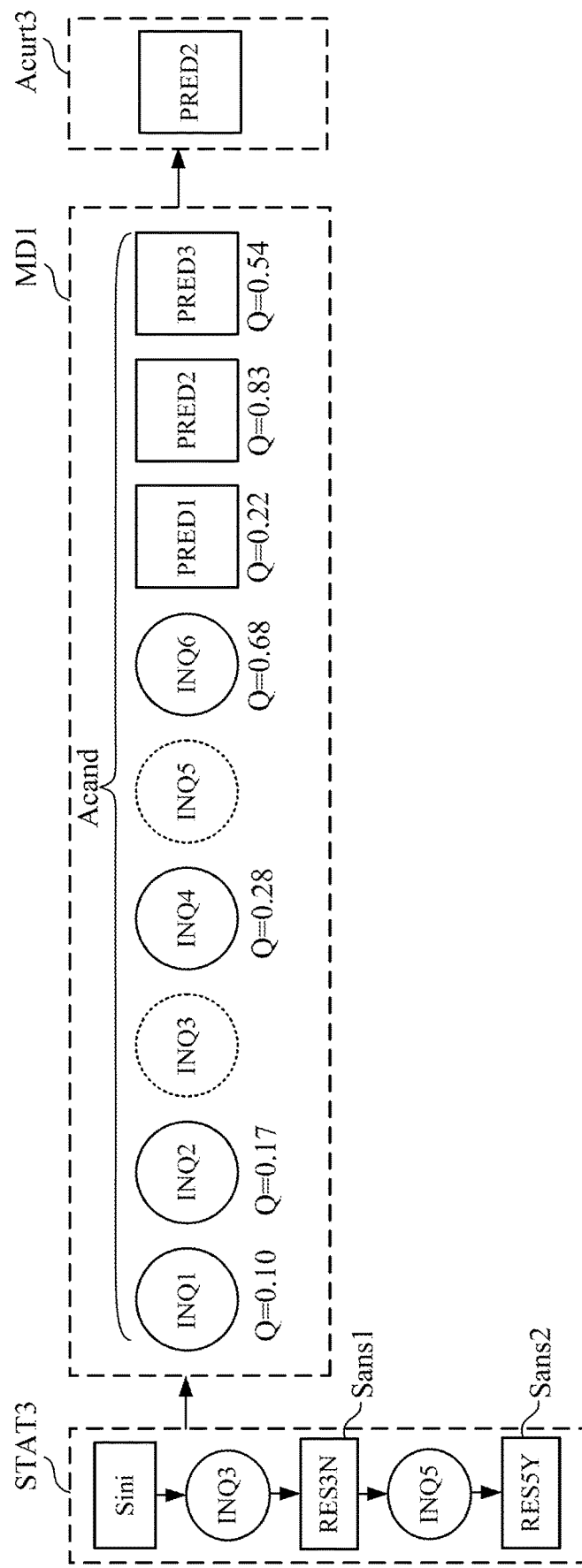

Reference is further made to FIG. 5A to FIG. 5C, which are schematic diagrams illustrating a demonstrational example about how to generate the actions in the series in different stages. It is assumed that the candidate prediction model MD1 is selected as the representative prediction model in the demonstrational example shown in FIG. 5A to FIG. 5C. In other cases, the representative prediction model can be replaced by other candidate prediction models and not limited to the candidate prediction model MD1.

FIG. 5A illustrates a schematic diagram of the representative prediction model (the candidate prediction model MD1) at a first stage. When a first action of the actions in the series is decided as shown in FIG. 5A, the step S231 is performed to collect a current state STAT1 inputted to the representative prediction model (i.e., the candidate prediction model MD1). At the first stage, the current state STAT1 includes the initial symptom Sini. Step S232 is performed to generate state-action values respectively for each of the candidate actions (including the inquiry actions INQ1-INQ6 and the disease prediction actions PRED1-PRED3) according to the current state.

In an embodiment, the state-action values of the candidate actions can be respectively evaluated by Q-value function. The state-action Q-value function can be defined as: $Q^\pi(s, a)$. The outcome of Q-value function can be referred to the expected return of performing an action "a" in a state "s", along with a policy $\pi$. The Q-value can be divided into a current reward and an expected Q-value in the following stages. The expected return is elevated by a reward signal corresponding to performing the action.

The medical system 100 and the computer aided medical method 200 consider the inquiry and diagnosis process as a sequential decision problem of an agent (i.e., the control circuit 120 based on the representative prediction model) that interacts with a patient. At each stage, the agent inquires a certain symptom of the patient. The patient then responds with true/false to the representative prediction model indicating whether the patient suffers from symptom. In the meantime, the agent can integrate user responses over time steps to propose subsequent questions. At the end of the process, the agent receives a scalar reward if it can correctly predict the disease with limited number of inquiries (every addition inquiry deduces a penalty from the reward). The goal of the agent is to maximize the reward. In other words, the goal is to correctly predict the patient disease by the end of the diagnosis process with limited number of inquiries.

Given a state s, the representative prediction model outputs the Q-value of each candidate actions. In our definition, there are two types of candidate actions, which are the inquiry actions INQ1-INQ6 and the disease prediction actions PRED1-PRED3. If the maximum Q-value of the outputs corresponds to one of the inquiry actions INQ1-INQ6, then the control circuit 120 outputs the corresponding symptom inquiry to the user U1, obtains a symptom response from the user U1, and proceeds to the next stage.

In the situation shown in FIG. 5A, the current state STAT1 including the initial symptom Sini merely provides a little information about the user U1. Currently, the information provided by the initial symptom Sini will not be enough to make the disease prediction. The medical system 100 and the computer aided medical method 200 will prefer to take an inquiry action rather than make the disease prediction at this stage. As shown in FIG. 5A, the Q-values of the inquiry actions INQ1-INQ6 will be relatively higher and the Q-values of the disease prediction actions PRED1-PRED3 will be relatively lower at the current stage.

Step S233 is performed by selecting one of the candidate actions with the highest one of the state-action values as the current action of the actions in the series. In the embodiment show in FIG. 5A, the inquiry action INQ3 has the highest Q-value (Q=0.45). Therefore, the inquiry action INQ3 is selected as the current action Acurt1, which is also the first action of the actions in the series.

Step S234 is performed to determine whether the current action Acurt1 is an inquiry action or not. In this case, the current action Acurt1 is the inquiry action INQ3, such that a symptom inquiry corresponding to the inquiry action INQ3 can be displayed on the interaction interface 140 in the step S235.

Reference is further made to FIG. 5B, which illustrates the schematic diagram of the representative prediction model (the candidate prediction model MD1) at a second stage after the first stage shown in FIG. 5A.

The step S231 is performed to collect a current state STAT2 inputted to the representative prediction model (i.e., the candidate prediction model MD1). At the second stage, the current state STAT2 includes the initial symptom Sini, the previous inquiry action INQ3 and the symptom response RES3N corresponding to the inquiry action INQ3. In this case, the symptom response RES3N indicates that the user U1 does not suffer the symptom mentioned in the inquiry action INQ3. Step S232 is performed again to generate state-action values respectively for each of the candidate actions (including the inquiry actions INQ1, INQ2, INQ4-INQ6 and the disease prediction actions PRED1-PRED3) according to the current state STAT2. The state-action values of the candidate actions will be updated according to the symptom response RES3N. In this case, because the current state STAT2 has been different from the previous state (STAT1 shown in FIG. 5A), the state-action values respectively for each of the candidate actions can be re-evaluated by Q-value function. The outcome of Q-value function may be increased or reduced according to the Yes/No answer in the symptom response RES3N. While selecting a target inquiry action (i.e., the inquiry action INQ3 in this case) from the candidate actions, one of the inquiry actions capable of inducing significant variations on Q-values of other candidate actions will be selected as the target inquiry action. After the symptom response RES3N is provided to the medical system 100 and the computer aided medical method 200, the Q-values of the inquiry actions INQ1, INQ2, INQ4-INQ6 and the disease prediction actions PRED1-PRED3 will change in response to the symptom response RES3N.

As the embodiment shown in FIG. 5B, the inquiry action INQ5 has the highest Q-value (Q=0.57). Therefore, the inquiry action INQ5 is selected as the current action Acurt2, which is also the second action of the actions in the series.

In this case, the current action Acurt2 (which is the inquiry action INQ5) next to a previous action (Acurt1 shown in FIG. 5A) is generated further according to the symptom response RES3N beside the initial symptom Sini.

Step S234 is performed to determine whether the current action Acurt2 is an inquiry action or not. In this case, the current action Acurt2 is the inquiry action INQ5, such that a symptom inquiry corresponding to the inquiry action INQ5 can be displayed on the interaction interface 140 in the step S235.

Reference is further made to FIG. 5C, which illustrates the schematic diagram of the representative prediction model (the candidate prediction model MD1) at a third stage after the second stage shown in FIG. 5B.

The step S231 is performed to collect a current state STAT3 inputted to the representative prediction model (i.e., the candidate prediction model MD1). At the second stage, the current state STAT3 includes the initial symptom Sini, the previous inquiry action INQ3, the symptom response RES3N, the previous inquiry action INQ5 and the symptom response RES5Y corresponding to the inquiry action INQ5. In this case, the symptom response RES5Y indicates that the user U1 suffers the symptom mentioned in the inquiry action INQ5. Step S232 is performed again to generate state-action values respectively for each of the candidate actions (including the inquiry actions INQ1, INQ2, INQ4, INQ6 and the disease prediction actions PRED1-PRED3) according to the current state STAT3. The state-action values of the candidate actions will be updated according to the symptom response RES3N and the symptom response RES5Y. In this case, because the current state STAT3 has been different from the previous state (i.e., STAT2), the state-action values respectively for each of the candidate actions can be re-evaluated by Q-value function. The outcome of Q-value function may be increased or reduced according to the Yes/No answer in the symptom response RES3N and the symptom response RES5Y. While selecting a target inquiry action (i.e., the inquiry action INQ5 in this case) from the candidate actions, one of the inquiry actions capable of inducing significant variations on Q-values of other candidate actions will be selected as the target inquiry action. After the symptom response RES5Y is provided to the medical system 100 and the computer aided medical method 200, the Q-values of the inquiry actions INQ1, INQ2, INQ4, INQ6 and the disease prediction actions PRED1-PRED3 will change in response to the symptom response RES5Y.

As the embodiment shown in FIG. 5C, the disease prediction action PRED2 has the highest Q-value (Q=0.83). Therefore, the disease prediction action PRED2 is selected as the current action Acurt3, which is also the third action of the actions in the series.

In the situation shown in FIG. 5C, the current state STAT3 includes the initial symptom Sini, the previous inquiry action INQ3, the symptom response RES3N, the previous inquiry action INQ5 and the symptom response RES5Y. In this case, the current state STAT3 may provide sufficient information to make the disease prediction. Therefore, the Q-values of the inquiry actions INQ1, INQ2, INQ4 and INQ6 will be relatively lower and the Q-values of the target disease prediction action PRED2 will be relatively higher at the current stage.

In this case, the current action Acurt3 (which is the disease prediction action PRED2) next to a previous action (Acurt2 shown in FIG. 5A) is generated further according to the symptom response RES5Y beside the initial symptom Sini and the symptom response RES3N.

Step S234 is performed to determine whether the current action Acurt3 is an inquiry action or not. In this case, the current action Acurt3 is not an inquiry action but the disease prediction action PRED2, such that step S240 is performed according to the disease prediction action PRED2.

In some embodiments, when the disease prediction action PRED2 is selected as the current action Acurt3, the computer aided medical method 200 further generates a prediction result in the step S240 according to the selected disease prediction action PRED2. In an embodiment, the prediction result can be a list of disease names ranked by probability. For example, the list of disease can include the disease prediction actions PRED2, PRED3 and PRED1 in a first ranking of their Q-values (0.83, 0.54 and 0.22 in the example shown in FIG. 5C). The first ranking of the disease prediction actions PRED2, PRED3 and PRED1 in step S240 is determined by the candidate prediction model MD1 according to the initial symptom input Sini and the symptom responses Sans corresponding to the symptom inquiries Sqry. The first ranking cannot reflect other information (e.g., gender, age, a historical medical record, a residence of the patient, a blood type of the patient or a DNA of the patient) besides symptoms of the patient and related information (location, current reason, current temperature at the disease prediction procedure) or medical event (e.g., a broadcast event of SARS, Zika virus or H1N1). In this embodiment as shown in FIG. 1, context information CON is also obtained through the interaction interface 140. The context information CON can include an age of the patient, a gender of the patient, a blood type of the patient, a DNA of the patient, a historical medical record of the patient, a residence of the patient, a current season, a current temperature, a location or a medical event when the disease prediction process is activated. In another embodiment, the context information CON can be obtained by the medical system 100 by downloading or fetching from a medical record database in a hospital or a medical organization.

Figure 6:
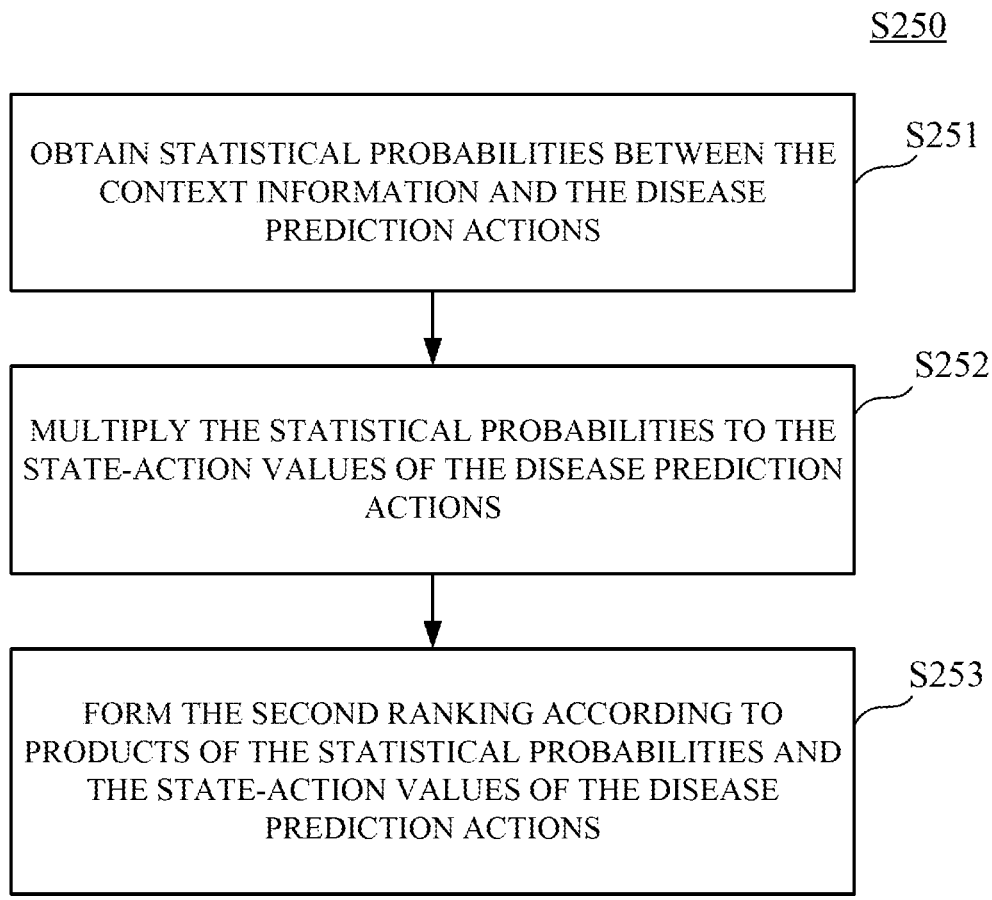
FIG. 6 is a flow chart illustrating further steps performed in one step in FIG. 2 according to an embodiment.

As shown in FIG. 2, step S250 is performed to adjust the first ranking into a second ranking according to the context information. Reference is further made to FIG. 6, which is a flow chart illustrating further steps S251-S253 performed in step S250 in FIG. 2 according to an embodiment. As shown in FIG. 6, step S251 is performed to obtain statistical probabilities between the context information and the disease prediction actions. The statistical probabilities can be fetched from Centers for Disease Control and Prevention or other medical databases.

A demonstrational example is provided in the following paragraphs to explain the step S250. In the demonstrational example, it is assumed that the context information indicates that the patient is a man whose age is between 45 and 59. The statistical probabilities show possibilities of diseases occurring to a man whose age is between 45 and 59 in general.

Step S252 is performed to multiply the statistical probabilities to the state-action values of the disease prediction actions. Afterward, step S253 is performed to form the second ranking according to products of the statistical probabilities and the state-action values of the disease prediction actions. Reference is made to the embodiment shown in FIG. 5C for demonstration. The first ranking of the disease prediction actions are PRED2, PRED3 and PRED1, it is assumed that the disease prediction actions are Urinary Tract Infection (PRED2), Kidney Stone (PRED3) and Temporary or Benign Blood in Urine (PRED1) in the first ranking determined by the candidate prediction model MD1.

According to the statistical probabilities to a man whose age is between 45 and 59 in general, a probability of Urinary Tract Infection is 2% (because the Urinary Tract Infection usually occurs to female patients), a probability of Kidney Stone is 25% (because the man whose age between 45 and 59 is highly risky to have a disease of Kidney Stone) and a probability of Temporary or Benign Blood in Urine is 20%. A product of the Q-value (0.83) of the Urinary Tract Infection (PRED2) and the probability (0.0166). A product of the Q-value (0.54) of the Kidney Stone (PRED3) and the probability (0.135). A product of the Q-value (0.22) of the Temporary or Benign Blood in Urine (PRED1) and the probability (0.044). In this case, the second rankings between disease prediction actions PRED1-PRED3 according to products of the statistical probabilities and the state-action values of the disease prediction actions will be PRED3, PRED1 and then PRED2 in the second rankings. Afterward, step S260 in FIG. 2 is performed to generate a list of the potential disease predictions in the second ranking. In this list, the disease prediction action PRED3 (Kidney Stone) will be ranked on top; the disease prediction action PRED1 (Temporary or Benign Blood in Urine) will be ranked at the second place; and then disease prediction action PRED2 (Urinary Tract Infection) will be ranked after these two diseases.

Another demonstrational example is provided in the following paragraph to explain the step S250. In the demonstrational example, it is assumed that the context information indicates that the patient is a woman whose age is above 75. The statistical probabilities show possibilities of diseases occurring to a woman whose age is above 75 in general. In this demonstrational example, the disease predictions at top 5 in the first ranking provided by one of the candidate prediction models are Metastatic cancer, Chronic constipation, Abdominal Hernia, Chronic Kidney Disease and Gastroesophageal Reflux Disease in the first ranking. Based on the statistical probabilities relative to the woman whose age is above 75, the disease predictions at top 5 in the second ranking are Osteoporosis, Metastatic cancer, Chronic Kidney Disease, Decubitus Ulcer and Venous Insufficiency. As shown in this demonstrational example, the disease prediction "Osteoporosis", which is not considered one of the top 5 possible diseases in the first ranking according to the symptom inquires, is listed on the first place in the second ranking, because "Osteoporosis" frequently occurs to elder woman.

Another demonstrational example is provided in the following paragraph to explain the step S250. In this demonstrational example, it is assumed that the context information indicates that the patient is an 80 years old man. In this demonstrational example, the disease predictions at top 5 in the first ranking provided by one of the candidate prediction models are Chronic Obstructive Pulmonary Disease (COPD), Atelectasis, Alzheimer Disease, Hypovolemia and Callus in the first ranking. After taking the context information for consideration (the patient is an 80 years old man), the disease predictions at top 5 in the second ranking are Alzheimer Disease, Chronic Obstructive Pulmonary Disease (COPD), Atelectasis, Hypovolemia and Callus. Before the context-aware transformation, the Alzheimer Disease is ranked at the third place in the predictions. The Alzheimer Disease gets boosted with context because Alzheimer disease is highly likely to happen in a patient older than 75.

Another demonstrational example is provided in the following paragraph to explain the step S250. In this demonstrational example, it is assumed that the context information indicates that the patient is 25 years old woman and the diagnostic happens in November. In this demonstrational example, the disease predictions at top 5 in the first ranking provided by one of the candidate prediction models are Chronic Obstructive Pulmonary Disease (COPD), Common Cold, Atelectasis, Lactose Intolerance and Callus in the first ranking. After taking the context information for consideration (the patient is 25 years old woman and the diagnostic happens in November), the disease predictions at top 5 in the second ranking are Common Cold, Chronic Obstructive Pulmonary Disease (COPD), Atelectasis, Lactose Intolerance and Callus. The common cold gets boosted with context because the context information indicates the current season is winter. The season makes the probability of common cold increase. So the prediction is corrected after context-aware transformation.

Based on four demonstrational examples above, the first ranking can be converted to the second ranking according to the context information including age of the patient, the gender of the patient and/or the current season of the disease prediction process. However, the context information is not limited thereto. The context information can include a historical medical record of the patient, a residence of the patient, a current temperature of the disease prediction process or any equivalent data about the patient or the environment surrounding the patient.

In some other approaches, the context information might be merged into the training data for establishing the candidate prediction models. In these approaches, if the medical system tends to add a new factor into the context information, all of the candidate prediction models must be trained again based on the context information including the newly added factor.

Based on aforesaid embodiments of the computer aided medical method 200 shown in FIG. 2, FIG. 4 and FIG. 6, the context information (e.g., age, gender, historical medical record, season factor, temperature) can be taken into consideration at the step S250 to re-arrange the ranking of the potential disease prediction, such that the disease prediction result generated by the computer aided medical method 200 can be adjusted according to the context information. If a new factor is added into the context information in the computer aided medical method 200, it is not necessary to train all of the candidate prediction models again.

Another embodiment of disclosure includes a non-transitory computer readable storage medium (e.g., the storage unit 160 shown in FIG. 1) with a computer program to execute aforesaid computer aided medical method 200 shown in FIG. 2, FIG. 4 and FIG. 6.

In aforesaid embodiment shown in FIG. 2, the computer aided medical method 200 selects the representative prediction model from the candidate prediction models MD1-MDn according to the initial symptom Sini. Afterward, the representative prediction model is utilized to complete the following prediction procedure. In the aforesaid embodiment shown in FIG. 2, the representative prediction model is a fixed one selected from the candidate prediction models MD1-MDn, wherein n is a positive integer. However, the disclosure is not limited thereto.

Figure 7:
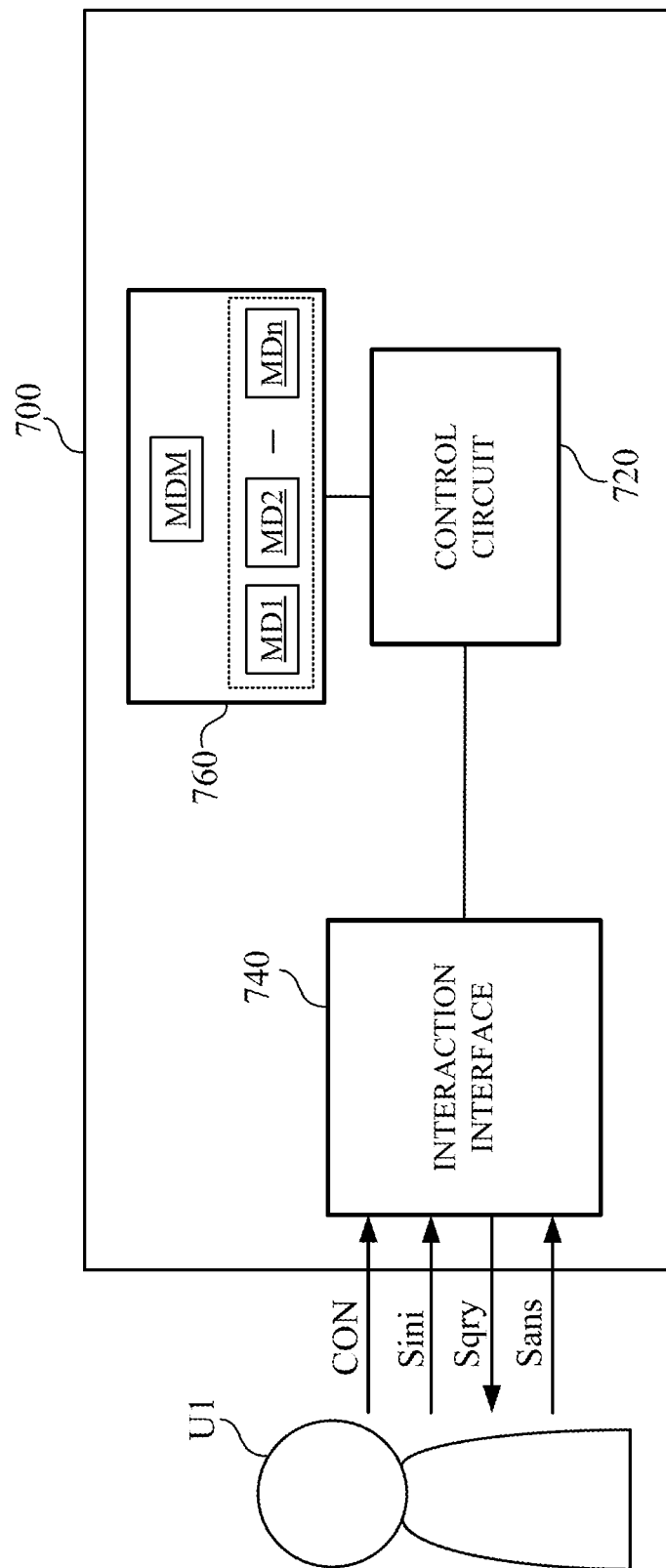
FIG. 7 is a schematic diagram illustrating a medical system according to an embodiment of the disclosure.

Reference is further made to FIG. 7, which is a schematic diagram illustrating a medical system 700 according to an embodiment of the disclosure. The medical system 700 includes a control circuit 720, an interaction interface 740 and a storage unit 760. A circuitry structure of the medical system 700 in FIG. 7 is similar to the circuitry structure of the medical system 100 in FIG. 1. In the embodiment of the medical system 700, there are multiple candidate prediction models MD1-MDn established and stored in the storage unit 760. Each of the candidate prediction models MD1-MDn is trained independently corresponding to different anatomical parts of a human body. Each of the candidate prediction models MD1-MDn is trained according to clinical data related to one anatomical part of the human body. The details of the candidate prediction models MD1-MDn are similar to aforesaid embodiment shown in FIG. 1. In this embodiment shown in FIG. 2, the medical system 700 further establishes a model-selection model MDM.

The model-selection model MDM is utilized to determine a dynamic prediction model from the candidate prediction models MD1-MDn to be responsible to generate each one of the actions in the series. In this embodiment, the dynamic prediction model can be re-determined by the model-selection model MDM corresponding to each one of the actions in the series. The first one of the actions in the series can be selected according to the candidate prediction model MD1 related to one part of the human body, and the second one of the actions in the series can be selected according to the candidate prediction model MDn related to another part of the human body. In this embodiment shown in FIG. 7, the actions in the series during the whole prediction procedure are not limited to be selected by the same candidate prediction model.

Figure 8:
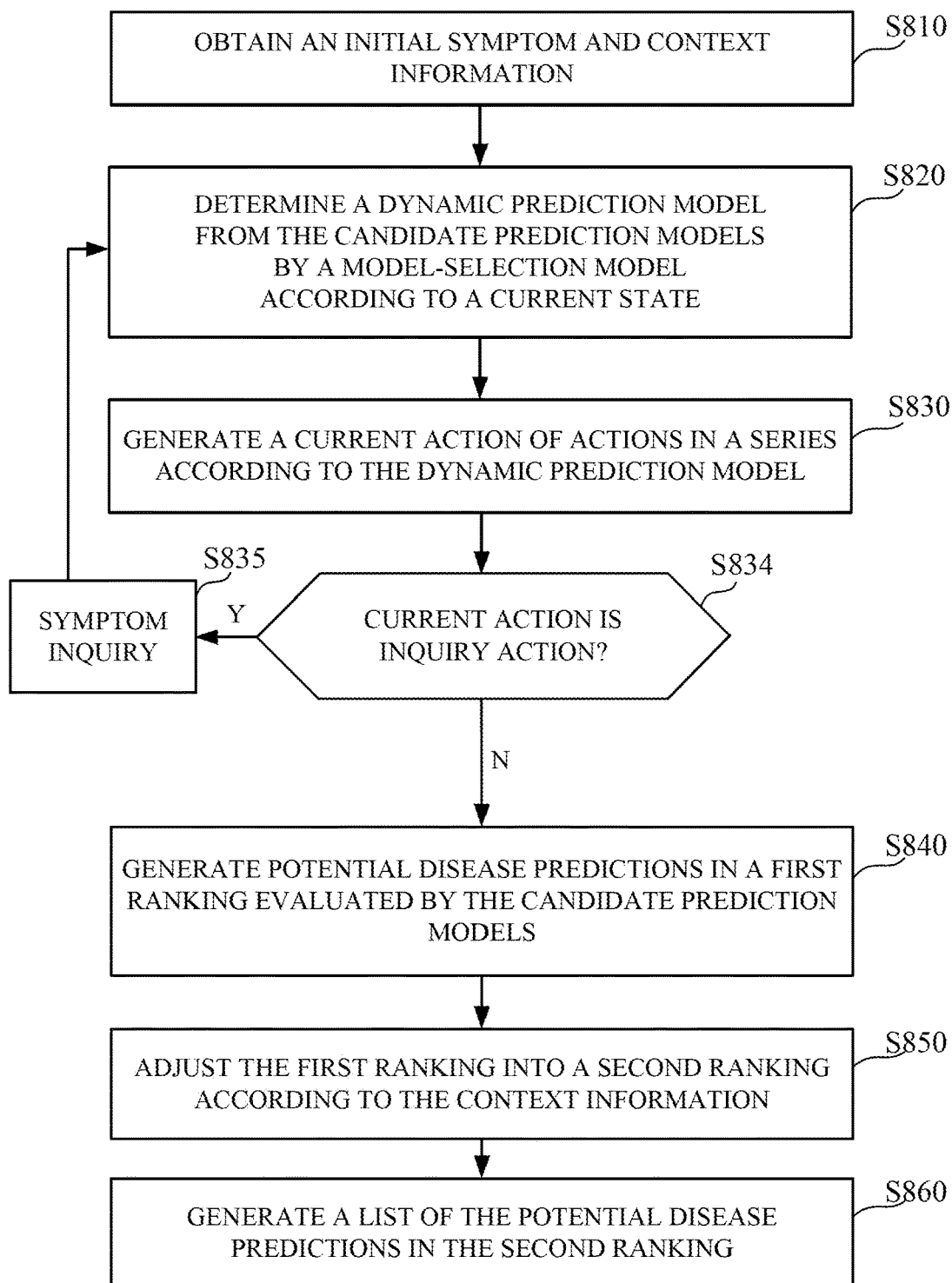
FIG. 8 is a flow chart illustrating a computer aided medical method according to an embodiment of the disclosure.

Reference is further made to FIG. 8, which is a flow chart illustrating a computer aided medical method 800 according to an embodiment of the disclosure. The computer aided medical method 800 is suitable to be utilized on the medical system 700 in FIG. 7.

Step S810 is performed to obtain an initial symptom Sini and context information Con. Step S820 is performed to determine a dynamic prediction model from the candidate prediction models MD1-MDn by the model-selection model MDM according to a current state. At the beginning, the current state only includes the initial symptom Sini. The model-selection model MDM is able to determine the dynamic prediction model from the candidate prediction models MD1-MDn according to the initial symptom Sini. Step S830 is performed to select a current action of the actions in the series according to the dynamic prediction model in this round. Step S830 can include further sub-steps, such as collecting a current state inputted to the dynamic prediction model, generating state-action values respectively for each of the candidate actions in the dynamic prediction model and selecting one of the candidate actions with a highest one of the state-action values as the current action of the actions in the series (can be referred to steps S231, S232 and S233 in FIG. 4 for further details).

Step S834 is performed to determine whether the current action selected by the dynamic prediction model in this round is an inquiry action or not. If the current action is the inquiry action, step S835 is performed to display a symptom inquiry and collect the symptom response Sans from the patient U1. Afterward, the computer aided medical method 800 executes step S820 again to determine the dynamic prediction model from the candidate prediction models MD1-MDn by the model-selection model MDM according to a updated current state (including the initial symptom Sini, the symptom inquiry Sqry in previous round, and the symptom response Sans to the symptom inquiry Sqry). The dynamic prediction model determined in the second round can be different from the previously-selected dynamic prediction model in the first round, or can also be the same as the previously-selected dynamic prediction model in the first round. Whether to change or keep the dynamic prediction model is decided by the model-selection model MDM. The model-selection model MDM is trained by the trained by the machine learning algorithm according to the clinical data. In the training process, the model-selection model MDM is able to make a decision of one dynamic prediction model from the in each round, and the model-selection model MDM will receive a positive reward signal when the final prediction is correct, and receive a negative feedback signal when the final prediction is wrong.

Steps S830-S835 will be repeated several rounds until one of the disease prediction actions in the dynamic prediction model is selected as the latest one of the actions in the series. When the disease prediction action is selected (e.g., step S834 will detect that the current action is not an inquiry action), step S840 is performed to generate potential disease predictions in a first ranking evaluated by the candidate prediction models. Step S850 is performed to adjust the first ranking into a second ranking according to the context information. Step S860 is performed to generate a list of the potential disease predictions in the second ranking. Details of steps S840-S860 in the computer aided medical method 800 are similar to steps S240-S260 in aforesaid embodiments shown in FIG. 2 and FIG. 6, and not to be repeated again.

Based on the computer aided medical method 800, different rounds of the disease prediction procedure may not all determine by the same candidate prediction model matching to the initial symptom Sini. In this embodiment, if the initial symptom Sini provided by the patient U1 is not ideal to describe the disease occurring to the patient U1, the computer aided medical method 800 still has a chance to switch to another candidate prediction model according to the following symptom response Sans. Therefore, the computer aided medical method 800 may refer to multiple candidate prediction models to make the diagnosis. The final prediction made by the computer aided medical method 800 is similar to a consultation of doctors from different medical departments. Therefore, the prediction made by the computer aided medical method 800 will have a better accuracy.

Another embodiment of disclosure includes a non-transitory computer readable storage medium (e.g., the storage unit 760 shown in FIG. 7) with a computer program to execute aforesaid computer aided medical method 800 shown in FIG. 8.

Figure 9:
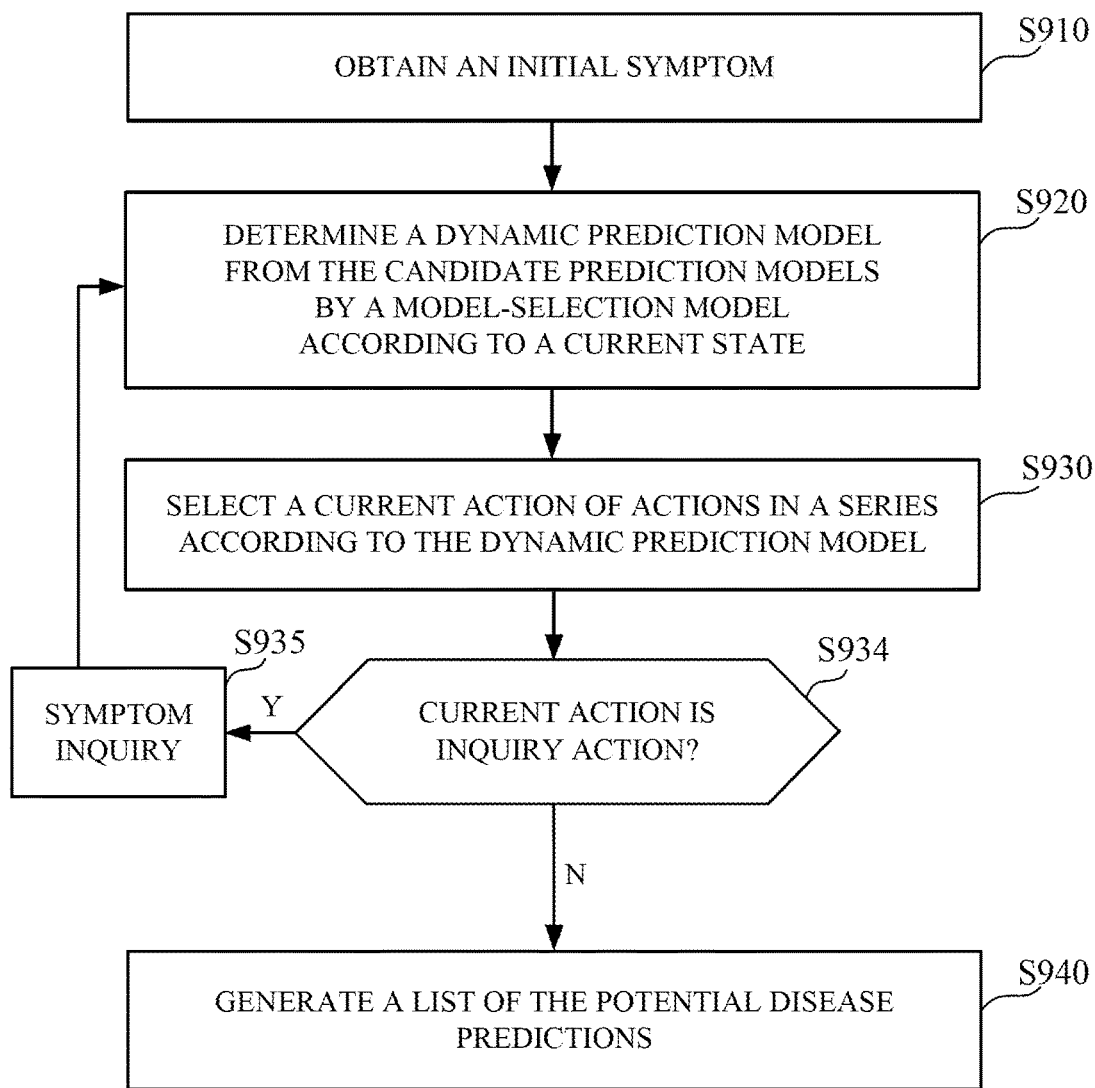
FIG. 9 is another flow chart illustrating a computer aided medical method according to an embodiment of the disclosure.

Reference is further made to FIG. 9, which is a flow chart illustrating a computer aided medical method 900 according to an embodiment of the disclosure. The computer aided medical method 900 is suitable to be utilized on the medical system 700 in FIG. 7.

Step S910 is performed to obtain an initial symptom Sini (e.g., one or more symptoms inputted by the user U1). In the embodiment of the computer aided medical method 900, the context information is not required. Step S920 is performed to determine a dynamic prediction model from the candidate prediction models MD1-MDn by the model-selection model MDM according to a current state. At the beginning, the current state only includes the initial symptom Sini. The model-selection model MDM is able to determine the dynamic prediction model from the candidate prediction models MD1-MDn according to the initial symptom Sini. Step S930 is performed to select a current action of the actions in the series according to the dynamic prediction model in this round. Step S930 can include further sub-steps, such as collecting a current state inputted to the dynamic prediction model, generating state-action values respectively for each of the candidate actions in the dynamic prediction model and selecting one of the candidate actions with a highest one of the state-action values as the current action of the actions in the series (can be referred to steps S231, S232 and S233 in FIG. 4 for further details).

Step S934 is performed to determine whether the current action selected by the dynamic prediction model in this round is an inquiry action or not. If the current action is the inquiry action, step S935 is performed to display a symptom inquiry and collect the symptom response Sans from the patient U1. Afterward, the computer aided medical method 900 executes step S920 again to determine the dynamic prediction model from the candidate prediction models MD1-MDn by the model-selection model MDM according to a updated current state. The dynamic prediction model determined in the second round can be different from the previously-selected dynamic prediction model in the first round, or can also be the same as the previously-selected dynamic prediction model in the first round. Whether to change or keep the dynamic prediction model is decided by the model-selection model MDM.

Steps S930-S935 will be repeated several rounds until one of the disease prediction actions in the dynamic prediction model is selected as the latest one of the actions in the series. When the disease prediction action is selected (e.g., step S934 will detect that the current action is not an inquiry action), step S940 is performed to generate a list of the potential disease predictions. The potential disease predictions in the list are arranged in a ranking evaluated by the candidate prediction models. The ranking evaluated by the candidate prediction models can be determined according to the Q-values of the disease prediction actions. For example, the list of potential disease predictions can include the disease prediction actions PRED2, PRED3 and PRED1 in the ranking of their Q-values (0.83, 0.54 and 0.22 in the example shown in FIG. 5C).

Based on the computer aided medical method 900, different rounds of the disease prediction procedure may not all determine by the same candidate prediction model matching to the initial symptom Sini. In this embodiment, if the initial symptom Sini provided by the patient U1 is not ideal to describe the disease occurring to the patient U1, the computer aided medical method 900 still has a chance to switch to another candidate prediction model according to the following symptom response Sans. Therefore, the computer aided medical method 900 may refer to multiple candidate prediction models to make the diagnosis. The final prediction made by the computer aided medical method 900 is similar to a consultation of doctors from different medical departments. Therefore, the prediction made by the computer aided medical method 900 will have a better accuracy.

Based on the above mentioned description, in one embodiment, the medical system 100 may directly generate the disease prediction action according to at least one initial symptom inputted by the user and one or more candidate prediction models without generating one or more inquiry actions.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A computer aided disease predicting method, based on a plurality of candidate prediction models each trained independently by a first machine learning algorithm according to first clinical data, each of the candidate prediction models comprises a plurality of inquiry actions and a plurality of disease prediction actions, the computer aided method comprising:
generating an interaction interface;
obtaining an initial symptom from the interaction interface;
obtaining context information, wherein the obtained context information is different from the obtained initial symptom, wherein the context information comprises a first context information;
sequentially generating a series of actions according to the candidate prediction models and the initial symptom and not according to the obtained first context information, each of the actions corresponding to one inquiry action or one disease prediction action;
in response to that the latest one of the sequential actions corresponding to one disease prediction action, generating a plurality of potential disease predictions in a first ranking evaluated by the candidate prediction models;
adjusting the first ranking into a second ranking according to the obtained first context information; and
generating a result prediction corresponding to the potential disease predictions in the second ranking.

2. The computer aided disease predicting method of claim 1, wherein the series of the actions are generated according to at least one of a dynamic prediction model determined and selected from the candidate prediction models by a model-selection model according to a current state, and the computer aided disease predicting method further comprises:
generating a plurality of state-action values respectively for each of candidate actions in the dynamic prediction model according to the current state; and
selecting one of the candidate actions in the dynamic prediction model with the highest one of the state-action values as a current action of the sequential actions.

3. The computer aided disease predicting method of claim 2, wherein the potential disease predictions in the first ranking is generated by:
ranking all of the disease prediction actions in the dynamic prediction model in order from high to low according to the state-action values of the disease prediction actions.

4. The computer aided disease predicting method of claim 3, wherein the first ranking is adjusted into the second ranking by:
obtaining a plurality of statistical probabilities between the first context information and the disease prediction actions;
multiplying the statistical probabilities to the state-action values of the disease prediction actions; and
forming the second ranking according to products of the statistical probabilities and the state-action values of the disease prediction actions.

5. The computer aided disease predicting method of claim 4, wherein the first context information comprises an age of the patient, a gender of the patient, a blood type of the patient, a DNA of the patient, a historical medical record of the patient, a residence of the patient, a current season, a current temperature, a location, or a medical event.

6. The computer aided disease predicting method of claim 2, wherein the dynamic prediction model is re-determined by the model-selection model corresponding to each of the sequential actions.

7. The computer aided disease predicting method of claim 2, further comprising:
in response to that one of the inquiry actions is selected as the current action of the sequential actions, collecting a symptom response corresponding to the one of the inquiry actions,
wherein a next action of the sequential actions is generated further according to the symptom response.

8. The computer aided disease predicting method of claim 7, wherein the current state comprises all of the inquiry actions and corresponding symptom responses prior to the current action.

9. The computer aided disease predicting method of claim 2, wherein the dynamic prediction model is determined by:

generating a plurality of state-model values respectively for each of the candidate prediction models; and selecting one of the candidate prediction models with a highest one of the state-model values as the dynamic prediction model to select the current action of the sequential actions.

10. The computer aided disease predicting method of claim 1, wherein the candidate prediction models are trained independently corresponding to different anatomical parts of a human body, each of the candidate prediction models is trained according to the first clinical data related to one anatomical part of the human body, the first clinical data comprises a plurality of clinical records, each of the clinical records describes a relationship between a diagnosed disease and corresponding symptoms of the diagnosed disease.

11. The computer aided disease predicting method of claim 1, further comprising:

receiving a reward and training the candidate prediction models to maximize the reward, wherein each time one of the inquiry actions is selected, a penalty is deduced from the reward, and a current action of the sequential actions is selected by:

generating a plurality of state-action values respectively for each of candidate actions according to the current state; and selecting one of the inquiry actions that is capable of inducing most variations on the state-action values of other candidate actions as the current action.

12. A non-transitory computer readable storage medium with a computer program to execute a computer aided disease predicting method, wherein the computer aided disease predicting method comprises:

generating an interaction interface;

obtaining an initial symptom of a patient from the interaction interface;

obtaining context information, wherein the obtained context information is different from the obtained initial symptom, wherein the context information comprises a first context information;

sequentially generating a series of actions according to the candidate prediction models and the initial symptom and not according to the obtained first context information, wherein each of the candidate prediction models is trained independently by a first machine learning algorithm according to first clinical data, and each of the actions corresponds to one inquiry action or one disease prediction action;

the disease prediction action, generating a plurality of potential disease predictions in a first ranking evaluated by the candidate prediction models;

adjusting the first ranking into a second ranking according to the obtained first context information; and generating a result prediction corresponding to the potential disease predictions in the second ranking.

13. The non-transitory computer readable storage medium of claim 12, wherein the computer aided disease predicting method further comprises:

receiving a reward and training the candidate prediction models to maximize the reward, wherein each time one of the inquiry actions is selected, a penalty is deduced from the reward, and a current action of the sequential actions is selected by:

generating a plurality of state-action values respectively for each of candidate actions according to the current state; and selecting one of the inquiry actions that is capable of inducing most variations on the state-action values of other candidate actions as the current action.

14. A medical system, based on a plurality of candidate prediction models each trained independently by a first machine learning algorithm according to first clinical data, each of the candidate prediction models comprises a plurality of inquiry actions and a plurality of disease prediction actions, the medical system comprising:

an interaction interface, configured for collecting an initial symptom; and a control circuit, communicated with the interaction interface, wherein the control circuit is operable to:

obtain context information, wherein the obtained context information is different from the obtained initial symptom, wherein the context information comprises a first context information;

sequentially generate a series of actions according to the candidate prediction models and the initial symptom and not according to the obtained first context information, and each of the actions corresponding to one inquiry action or one disease prediction action;

the disease prediction action, generate a plurality of potential disease predictions in a first ranking evaluated by the candidate prediction models;

adjust the first ranking into a second ranking according to the obtained first context information; and generate a result prediction corresponding to the potential disease predictions in the second ranking.

15. The medical system of claim 14, wherein the control circuit determines a dynamic prediction model from the candidate prediction models by a model-selection model according to a current state, the control circuit generates a plurality of state-action values respectively for each of the candidate actions in the dynamic prediction model according to the current state, the control circuit selects one of the candidate actions in the dynamic prediction model with a highest one of the state-action values as a current action of the sequential actions.

16. The medical system of claim 15, wherein the control circuit ranks all of the disease prediction actions in the dynamic prediction model in order from high to low according to the state-action values of the disease prediction actions, so as to generate the potential disease predictions in the first ranking.

17. The medical system of claim 16, wherein the control circuit obtains a plurality of statistical probabilities between the obtained first context information and the disease prediction actions, the control circuit multiplies the statistical probabilities to the state-action values of the disease prediction actions, the control circuit forms the second ranking according to products of the statistical probabilities and the state-action values of the disease prediction actions.

18. The medical system of claim 17, wherein the obtained first context information comprises an age of the patient, a gender of the patient, a blood type of the patient, a DNA of the patient, a historical medical record of the patient, a residence of the patient, a current season, a current temperature, a location or a medical event.

19. The medical system of claim 15, wherein the control circuit re-determines the dynamic prediction model according to the model-selection model corresponding to each of the sequential actions.

20. The medical system of claim 14, wherein the control circuit receives a reward and trains the candidate prediction models to maximize the reward, wherein each time one of the inquiry actions is selected, a penalty is deduced from the reward, and a current action of the sequential actions is selected by:
  generating a plurality of state-action values respectively for each of candidate actions according to the current state; and
  selecting one of the inquiry actions that is capable of inducing most variations on the state-action values of other candidate actions as the current action.

* * * * *